United States Patent [19]

Curtze et al.

[11] Patent Number: 5,495,019
[45] Date of Patent: Feb. 27, 1996

[54] PROCESS FOR THE PREPARATION OF 3,3-DIARYL ACRYLIC ACID AMIDES

[75] Inventors: Jurgen Curtze, Johannisberg; Bodo Haertel, Ingelheim, both of Germany

[73] Assignee: American Cyanamid Company, Wayne, N.J.

[21] Appl. No.: 362,450

[22] PCT Filed: Jul. 8, 1993

[86] PCT No.: PCT/EP93/01803

§ 371 Date: Mar. 16, 1995

§ 102(e) Date: Mar. 16, 1995

[87] PCT Pub. No.: WO94/14241

PCT Pub. Date: Jan. 20, 1994

[51] Int. Cl.⁶ .................... C07D 295/192; C07C 231/12
[52] U.S. Cl. .................... 544/174; 544/165; 544/176; 564/171
[58] Field of Search .................... 544/165, 174, 544/176; 564/171

[56] References Cited

FOREIGN PATENT DOCUMENTS

| 219756 | 4/1987 | European Pat. Off. |
| 294907 | 12/1988 | European Pat. Off. |
| 329256 | 8/1989 | European Pat. Off. |
| 343743 | 11/1989 | European Pat. Off. |

OTHER PUBLICATIONS

Chodkiewicz, "Preparation d'amides et de nitriles beta–alcools diaryles; deshydratation en derives alpha–ethyleniques correspondants", Bulletin De La Societe Chimique De France, pp. 1586–1591, Paris, France 1958.

*Primary Examiner*—Robert W. Ramsuer
*Attorney, Agent, or Firm*—Gregory M. Hill

[57] ABSTRACT

The invention provides a process for the preparation of 3,3-diaryl acrylic acid amides of the general formula

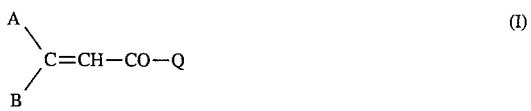

in which A, B and Q are as defined in the specification, by condensing a compound of formula

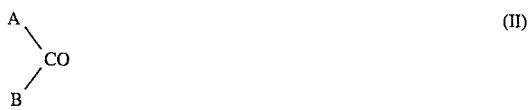

with a compound of formula

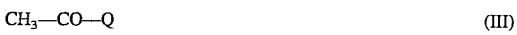

in which Q has the meaning given above, in a solvent in the presence of an alkali metal hydroxide, characterised in that the solvent is selected from alkanes, cycloalkanes or mixtures thereof.

9 Claims, No Drawings

PROCESS FOR THE PREPARATION OF 3,3-DIARYL ACRYLIC ACID AMIDES

This application is a 371 of PCT/EP93/01803 filed Jul. 8, 1993.

The invention concerns a new process for the preparation of 3,3-diaryl acrylic acid amides of the general formula I

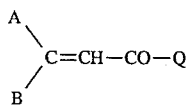

in which
A represents

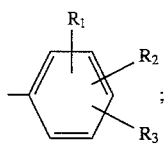

B represents

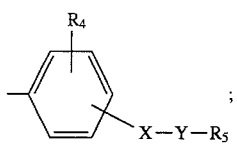

and
Q represents

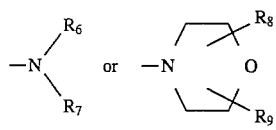

where
$R_1$ represents a $C_{1-4}$ alkyl, $C_{1-4}$ alkoxy, amino, mono- or di-($C_{1-4}$ alkyl)amino, $C_{2-4}$ alkenyl, $C_{3-4}$ alkynyl, $C_{3-4}$ alkenyloxy, $C_{3-4}$ alkynyloxy or $C_{3-6}$ cycloalkyl group;

$R_2$ represents a $C_{1-4}$ alkyl or $C_{1-4}$ alkoxy group or a halogen atom;

$R_3$ represents a hydrogen or halogen atom;

$R_4$ represents a hydrogen or halogen atom or a $C_{1-4}$ alkyl or $C_{1-4}$ alkoxy group;

$R_5$ represents a hydrogen atom, a phenyl group optionally substituted by one or more substituents selected from $C_{1-4}$ alkyl, $C_{1-4}$ alkoxy, halogen, phenyl and phenoxy moieties, a $C_{1-12}$ alkyl group optionally substituted by one or more halogen atoms, a $C_{3-7}$ cycloalkyl group, a $C_{2-6}$ alkenyl or a $C_{2-6}$ alkynyl group each optionally substituted by a phenyl group, or a naphthyl or $C_{5-8}$ cycloalkenyl group;

—X—Y— represents a single bond or a —O—, —S(O)$_p$—, —N═N—, —CHR$_{10}$—O—, —O—CHR$_{10}$—, —CHR$_{10}$—S(O)$_p$—, —S(O)$_p$—CHR$_{10}$—, —C$_n$H$_{2n}$—, —HC═CH— or —C≡C— moiety, in which moieties p represents 0, 1 or 2 and n represents an integer from 1 to 10;

$R_6$ represents a $C_{1-4}$ alkyl, $C_{3-7}$ cycloalkyl, benzyl, $C_{3-4}$ alkenyl or $C_{3-4}$ alkynyl group;

$R_7$ represents a $C_{1-4}$ alkyl group;

$R_8$ represents a hydrogen atom or a $C_{1-4}$ alkyl or $C_{1-4}$ alkoxy group; and $R_9$ and $R_{10}$ independently represent a hydrogen atom or a $C_{1-4}$ alkyl group.

Compounds of formula I are fungicidally active and are particularly useful in the control of phytopathogenic fungi, especially *Plasmopara viticola* and *Phytophthora infestans*. Particularly preferred compounds of formula I in this respect are those in which A represents a 3,4-dimethoxyphenyl, 3-ethoxy-4-methoxyphenyl, 3-chloro-4-methoxyphenyl, 3-bromo-4-methoxyphenyl, 3-methyl-4-methoxyphenyl, 3-ethyl-4-methoxyphenyl, 3-propyl-4-methoxyphenyl, 3,4-dimethylphenyl, 3-amino-4-methoxyphenyl, 3,5-dichloro-4-aminophenyl or 3-methoxy-4-methylphenyl group and, of these, 3,4-dimethoxyphenyl is especially preferred, and B represents 4-chlorophenyl or 4-(4-chlorophenoxy)phenyl. It is also preferred that Q represents a morpholino group. Especially preferred compounds of the general formula I are 3-(4-chlorophenyl)-3-(3,4-dimethoxyphenyl) acrylic acid morpholide and 3-[4-(4-chlorophenoxy)phenyl]-3-(3,4-dimethoxyphenyl) acrylic acid morpholide.

Compounds of the general formula I as well as processes for their preparation have been described in European patent applications EP 120 321 and EP 219 756.

A more efficient process for the preparation of compounds of the general formula I has been described in European patent application EP 294 907. In this document the condensation of a substituted benzophenone and an appropriate acetamide has been described in the presence of a strong base such as potassium tert-butylate, an alkali metal hydroxide or carbonate, or tert-butyl lithium. However, these methods give yields of less than 50%, due to decomposition of the starting materials and/or the end product under the influence of the base. Further, sometimes an intermediate is formed which has to be converted in a second step.

European patent application EP 329256 reveals that the yield of the above condensation reaction is considerably improved if a sodium tertiary alcoholate is used as the base. Such alcoholates react readily with the water which is produced in the course of the reaction yielding the corresponding alcohol and sodium hydroxide. This hydroxide, together with the alcoholate, in turn cleaves base-sensitive reactants, especially the acetamide, or the desired product, often to a large extent and thus reduces the yield from the process. Attempts to overcome this problem involved the use of a substantial excess, generally 3-fold or even higher, of the acetamide reactant. The use of expensive sodium tertiary alcoholates, which are made by reaction of sodium or sodium hydride and a tertiary alcohol in a relatively dangerous reaction, and the use of large amounts of acetamides, however, still give possibilities for further improvement of the reaction.

In European patent application EP 343 743 it has been described that the above described cleavage reaction of the acetamide compounds can be suppressed by the addition of an alkali metal mono-alkyl carbonate to the reaction mixture, thereby reducing the need for excess acetamide reactant to only a small excess, and increasing the purity of the products to nearly 100%.

It will be appreciated, however that there is still a need for an improved synthesis for the compounds of the general formula I, as the base used in the process according to European patent application EP 343 743 is expensive in view of the safety measures which have to be taken during the production of the tertiary alcoholates, while also the added alkali metal mono-alkyl carbonate increases the costs of the reaction.

It has now been found that the compounds of the general formula I can be made in high yields and high purities in a one step process using cheap sodium hydroxide as base and without using any auxiliary reagents by carrying out the reaction in alkanes as solvent. It will be appreciated that the use of commercially available sodium hydroxide avoids possible risks in the preparation of the above mentioned alkali metal tertiary alcoholates.

The present invention therefore relates to a process for the preparation of a compound of the general formula I in which A, B and Q are defined as above, by condensing a compound of the general formula II

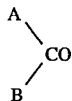

in which A and B have the meanings given above, with a compound of the general formula III

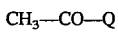

in which Q has the meaning given above, in a solvent in the presence of an alkali metal hydroxide, characterised in that the solvent is selected from alkanes, cycloalkanes or mixtures thereof.

Suitable alkanes and cycloalkanes for the process of the present invention are alkanes or cycloalkanes containing from 5 to 16 carbon atoms, especially alkanes or cycloalkanes containing from 6 to 12 carbon atoms or mixtures thereof. Preferably the alkane or cycloalkane contains 7 or 8 carbon atoms, and more preferably the alkane is n-heptane or n-octane. Suitable alkanes are also alkane distillation fractions with a specified boiling range. A suitable cycloalkane is cyclohexane.

The process according to the invention is suitably carried out using sodium or potassium hydroxide, preferably sodium hydroxide. The alkali metal hydroxide is suitably used as powder. It is also possible to start with an aqueous solution of sodium hydroxide together with an organic solvent which forms an azeotrope with water, from which aqueous solution the water is removed azeotropically. The amount of alkali metal hydroxide is suitably between 0.1 and 3 equivalent based on starting benzophenone, preferably between 0.7 and 1.8 equivalent.

The process according to the present invention is suitably carried out at a temperature from room temperature to the reflux temperature of the reaction mixture. Preferably the reaction temperature is between 80° C. and 160° C., more preferably between 100° C. and 150° C. The reaction time is usually between 1 and 48 hours, depending on the reaction temperature.

The amount of acetamide in the reaction according to the present invention is suitably between 1 and 6 equivalents based on starting benzophenone compound, preferably between 1.5 and 5, more preferably between 2.0 and 4.

The volume of solvent is suitably between a quarter of the volume of the starting products up to 100 times the volume of the starting materials, although more or less is also possible.

In a preferred embodiment of the invention the water, which is formed during the reaction is removed azeotropically from the reaction mixture. In the case of very high boiling alkanes or cycloalkanes the water may be removed by carrying out the reaction under diminished pressure.

In those cases in which it would be of advantage to obtain a solution of the end-product in an aromatic compound (for further work-up and/or processing) it is preferred to add a certain amount of that aromatic compound to the reaction mixture. Distillation of the alkane or cycloalkane will then result in a solution of the product in the aromatic compound. Therefore, another aspect of the invention is the addition of an aromatic compound to the reaction mixture, suitably up to 60% v/v with respect to the volume of the alkane solvent, preferably up to 40% v/v more preferably up to 20% v/v. Suitable aromatic compounds are toluene, xylene, mesitylene and mixtures thereof, such as commercially available mixtures of aromatics.

Compounds of formula II and formula III are either known compounds or can be produced from known compounds by known methods. In this respect reference is made to the above cited literature citations.

The process of the invention is illustrated by the following specific examples.

EXAMPLE 1

3-(4-Chlorophenyl)-3-(3,4-dimethoxyphenyl)-acrylic acid morpholide

4-Chloro-3', 4'-dimethoxybenzophenone (27.67 g; 0.1 mol), acetyl morpholide (38.75 g; 0.3 mol) and sodium hydroxide (4.00 g; 0.1 mol) in n-octane (80 ml) were refluxed under stirring for 10 hours. Subsequently, a part of the solvent (65 ml) was removed by distillation, toluene (160 ml) was added, the mixture heated to 80° C. and the resulting solution was washed twice with water (100 ml each). The organic layer was separated, dried and filled up to 500 mi. 3-(4-Chlorophenyl)-3-(3,4-dimethoxyphenyl)-acrylic acid morpholide was not isolated, the content was analytically determined to be 12.77 g. Additionally, the starting material (ketone) was found (16.92 g; 61.3%). Yield: 85% of the title compound (based on converted material).

EXAMPLE 2

3-(4-Chlorophenyl)-3-(3,4-dimethoxyphenyl)-acrylic acid morpholide

4-Chloro-3', 4'-dimethoxybenzophenone (27.67 g; 0.1 mol), acetyl morpholide (38.75 g; 0.3 mol) and sodium hydroxide (4.00 g; 0.1 mol) in a mixture of n-octane (40 ml) and mesitylene (40 ml) were refluxed under stirring for 10 hours. The refluxing condensate was passed through a column packed with molecular sieves (4 A; 10 g). Subsequently, a part of the solvent (20 ml) was removed with a rotary evaporator, the remaining mixture was made up to 100 ml with toluene, heated to 80° C. and washed twice with water (100 ml each). The organic layer was separated, and dried by azeotropic distillation of a part of the solvent (50 ml) with a rotary evaporator. Petrol ether (100 ml; bp. 58°–63° C.) was slowly added under stirring and the mixture was stirred for another hour at room temperature. The crystals were collected by vacuum filtration washed with toluene/petrol ether (1:3; 100 ml) and dried. Yield: 28.2 g (72.7%). Purity: 98.4%. Mp.: 128°–147° C. The mother liquor contained an additional 2.31 g of compound, thus, the total yield of pure compound was 77.5%.

EXAMPLE 3

3-(4-Chlorophenyl)-3-(3,4-dimethoxyphenyl)-acrylic acid morpholide

4-Chloro-3', 4'-dimethoxybenzophenone (27.67 g; 0.1 mol), acetyl morpholide (38.75 g; 0.3 mol) and sodium hydroxide (4.00 g; 0.1 mol) in n-octane (80 ml) were refluxed for 10 hours. The refluxing condensate was passed through a column packed with molecular sieves (4 A, 10 g; can be replaced by a mixture of anhydrous sodium sulphate and sea sand). Subsequently, n-octane (30 ml) was distilled off and toluene (150 ml) was added. The mixture was heated to 80° C. and extracted twice with water (100 ml each). The organic layer was separated, and dried by azeotropic distillation of a part of the solvent (70 ml). The solution was kept at 40° C. and petrol ether (100 ml, bp. 58°–63° C.) was added in 15 minutes under stirring the mixture cooled to room temperature and stirred for another hour. The crystals were collected by vacuum filtration washed with toluene/petrol ether (1:3; 100 ml) and dried. Yield: 30.35 g (78.2%). Purity: 100%. Mp.:137°–154° C. The mother liquor contained an additional 1.35 g of compound, thus, the total yield of pure compound was 81.7% of th..

EXAMPLE 4

3-(4-Chlorophenyl)-3-(3,4-dimethoxyphenyl)-acrylic acid morpholide

4-Chloro-3', 4'-dimethoxybenzophenone (276.7 g; 1 mol), N-acetyl morpholine (387.6 g; 3 mol) and powdered sodium hydroxide (40.0 g; 1 mol) in n-octane (600 ml) were refluxed under stirring for 10 hours at a column internal temperature of 127° C. The refluxing condensate (3 l/h) was passed through a column packed with molecular sieves (4 A, 150 g). Subsequently, n-octane (450 ml) was distilled off and toluene (1 l) was added. The mixture was heated to 80° C. and extracted once with 500 ml water and twice with 250 ml water. The organic layer was separated, and dried by azeotropic distillation of a part of the solvent (125 ml) under reduced pressure. On cooling to room temperature, crystallisation already started. Under continuous stirring, 750 ml petroleum ether (bp. 58°–63° C.) was added over a period of 30 minutes. After standing overnight, the crystals were collected by vacuum filtration washed with toluene/petroleum ether (1:3; 400 ml) and dried. Yield: 268 g (69.1%). Mp.: 140°–152° C. The product was 98.1% pure and contained 0.9% of the original ketone. The mother liquor contained an additional 25.2 g of the title compound and 42.2 g of the original ketone. The water washings contained 207 g = 1.6 mol N-acetyl morpholine.

EXAMPLE 5

3-(4-Chlorophenyl)-3-(3,4-dimethoxyphenyl)-acrylic acid morpholide

4-Chloro-3', 4'-dimethoxybenzophenone (6.92 g; 25 mmol), acetyl morpholide (11.3 g; 87.5 mmol) and potassium hydroxide (1.65 g; 25 mmol; purity (85%) in cyclohexane (40 ml) were refluxed under stirring for 24 hours. The refluxing condensate was passed through a column packed with molecular sieve (4 A; 10 g). The cyclohexane was removed using a rotary evaporator, toluene (50 ml) was added, the mixture heated to 80° C. and extracted with water (40 ml each) twice. The organic layer was separated, and dried by azeotropic distillation of a part of the solvent (27 ml) with a rotary evaporator. Petrol ether (40 ml; bp. 58°–63° C.) was slowly added, whereupon 3-(4-chlorophenyl)-3-(3,4-dimethoxyphenyl)-acrylic acid morpholide crystallised. The precipitate was collected by vacuum filtration after 1 hour, washed with toluene/petrol ether (1:3; 20 ml) and dried. Yield: 7.6 g (78.48% of th.). Purity: 97.2%. Mp.: 139°–157° C. The mother liquor contained an additional 0.25 g of compound, thus, the total yield of pure compound was 78.8% of th..

We claim:

1. A process for the preparation of a compound of the general formula I

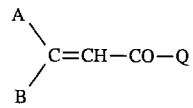

in which

A represents

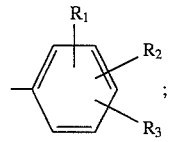

B represents

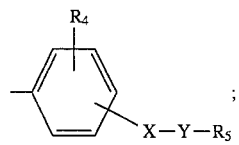

and

Q represents

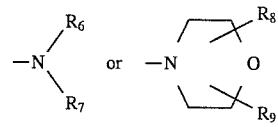

where $R_1$ represents a $C_{1-4}$ alkyl, $C_{1-4}$ alkoxy, amino, mono- or di-($C_{1-4}$ alkyl)amino, $C_{2-4}$ alkenyl, $C_{3-4}$ alkynyl, $C_{3-4}$ alkenyloxy, $C_{3-4}$ alkynyloxy or $C_{3-6}$ cycloalkyl group;

$R_2$ represents a $C_{1-4}$ alkyl or $C_{1-4}$ alkoxy group or a halogen atom;

$R_3$ represents a hydrogen or halogen atom;

$R_4$ represents a hydrogen or halogen atom or a $C_{1-4}$ alkyl or $C_{1-4}$ alkoxy group;

$R_5$ represents a hydrogen atom, a phenyl group optionally substituted by one or more substituents selected from $C_{1-4}$ alkyl, $C_{1-4}$ alkoxy, halogen, phenyl and phenoxy moieties, a $C_{1-12}$ alkyl group optionally substituted by one or more halogen atoms, a $C_{3-7}$ cycloalkyl group, a $C_{2-6}$ alkenyl or a $C_{2-6}$ alkynyl group each optionally substituted by a phenyl group, or a naphthyl or $C_{5-8}$ cycloalkenyl group;

—X—Y— represents a single bond or a —O—, —S(O)$_p$—, —N=N—, —CHR$_{10}$—O—, —O—CHR$_{10}$—, —CHR$_{10}$—S(O)$_p$—, —S(O)$_p$—CHR$_{10}$—, —C$_n$H$_{2n}$—, —HC=CH— or —C≡C— moiety, in which moieties p represents 0, 1 or 2 and n represents an integer from 1 to 10;

$R_6$ represents a $C_{1-4}$ alkyl, $C_{3-7}$ cycloalkyl, benzyl, $C_{3-4}$ alkenyl or $C_{3-4}$ alkynyl group;

$R_7$ represents a $C_{1-4}$ alkyl group;

$R_8$ represents a hydrogen atom or a $C_{1-4}$ alkyl or $C_{1-4}$ alkoxy group; and $R_9$ and $R_{10}$ independently represent a hydrogen atom or a $C_{1-4}$ alkyl group.

by condensing a compound of the general formula II

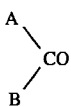

$$\text{II}$$

in which A and B have the meanings given above, with a compound of the general formula III

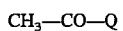   III in which Q has the meaning given above, in a solvent in the presence of an alkali metal hydroxide, characterised in that the solvent is selected from alkanes, cycloalkanes or mixtures thereof.

2. A process according to claim 1, in which the alkane or cycloalkane contains from 5 to 16 carbon atoms.

3. A process according to claim 2, in which the alkane or cycloalkane contains from 6 to 12 carbon atoms.

4. A process according to claim 3, in which the alkane or cycloalkane contains 7 or 8 carbon atoms.

5. A process according to claim 4 in which the alkane is n-heptane or n-octane.

6. A process according to claim 1, in which the alkali metal hydroxide is sodium or potassium hydroxide.

7. A process according to claim 1, in which water is removed azeotropically from the reaction mixture.

8. A process according to claim 1, in which an aromatic compound is added to the reaction mixture.

9. A process according to claim 1, in which the condensation reaction is carried out at a temperature from room temperature to the reflux temperature of the reaction mixture.

* * * * *